(12) United States Patent
Hennig

(10) Patent No.: US 6,328,748 B1
(45) Date of Patent: Dec. 11, 2001

(54) DEVICE AND METHOD FOR SETTING STEREOTACTIC AND ENDOSCOPICALLY PLACED EQUIPMENT

(75) Inventor: Rune Hennig, Tromsø (NO)

(73) Assignee: Elekta AB (publ.), Stockholm (SE)

( * ) Notice: Subject to any disclaimer, the term of this patent is extended or adjusted under 35 U.S.C. 154(b) by 0 days.

(21) Appl. No.: 09/508,629

(22) PCT Filed: Sep. 15, 1998

(86) PCT No.: PCT/NO98/00276

§ 371 Date: Jul. 20, 2000

§ 102(e) Date: Jul. 20, 2000

(87) PCT Pub. No.: WO99/16374

PCT Pub. Date: Apr. 8, 1999

(30) Foreign Application Priority Data

Sep. 16, 1997 (NO) .................................. 974274

(51) Int. Cl.⁷ .................................. A61B 19/00
(52) U.S. Cl. .................................. 606/130
(58) Field of Search .................................. 606/130, 1

(56) References Cited

U.S. PATENT DOCUMENTS

| | | |
|---|---|---|
| 2,697,433 * | 12/1954 | Zehnder .............................. 606/130 |
| 3,017,887 * | 1/1962 | Heyer .................................. 606/130 |
| 3,021,842 | 2/1962 | Flood . |
| 3,115,140 | 12/1963 | Volkman . |
| 4,681,103 | 7/1987 | Boner et al. . |
| 4,809,694 | 3/1989 | Ferrara . |
| 4,955,891 | 9/1990 | Carol . |
| 5,263,956 | 11/1993 | Nobles . |

* cited by examiner

Primary Examiner—Jeffrey A. Smith
Assistant Examiner—Eduardo C. Robert
(74) Attorney, Agent, or Firm—Finnegan, Henderson, Farabow, Garrett & Dunnerr, L.L.P.

(57) ABSTRACT

The invention concerns a device for adjusting stereotactically and endoscopically located equipment, including pharmaceutical agents, radiation sources and organic material, comprising a holder and a fixing key, where the holder comprises a lower ring (1) for receiving a ball (2) which will form a ball joint, and an upper ring (3) for locking the ball in a specific position, where the ball (2) has a channel for insertion of medical instruments, and where the lower ring (1) has an external threaded surface (8) for direct screwing to an area of a patient's skull. The device is characterized by the fact that the ball's (2) central point, and thereby the ball joint's fulcrum is arranged for positioning on a level with the patient's cranium by way of a groove-like or curved surface (21) on the holder which forms an abutment for the ball (2). The invention also concerns a method for adjusting different stereotactically and endoscopically located equipment, including pharmaceutical agents, by means of the device, and application of the method in different contexts.

15 Claims, 5 Drawing Sheets

DEVICE AND METHOD FOR SETTING STEREOTACTIC AND ENDOSCOPICALLY PLACED EQUIPMENT

The present invention concerns a device for adjustment of different stereotactically and endoscopically located equipment, including pharmaceutical agents, radiation sources and organic material and a method for adjustment of stereotactically and endoscopically located equipment.

Brain surgery procedures, where precise placement of instruments or other aids is required, are generally performed in several steps:

1. X-rays are taken of the patient.
2. The patient's head is firmly screwed to a frame which is provided with position indicators (stereotactic frame).
3. New X-rays are taken where markers on the frame permit calculations to be performed, thus enabling aids to be inserted into a desired area.
4. The patient is taken to the operating theatre.

An essential condition for the use of all such instrumentation with present day equipment is that the patient's head is fixed to the stereotactic equipment. The frame is usually attached by screws to the skullbone. The head is then fixed by means of arm devices, usually to the operating table.

U.S. Pat. No. 5,263,956 concerns a device for use in neurosurgery. A ball joint is arranged to hold a neurosurgery tool in a predetermined orientation relative to the patient's skull. A plate with sharpened corners is placed against the skull. The plate has a recess in which a ball joint is placed. A bore passes through the ball joint, permitting the introduction of neurosurgery equipment. The ball can be rotated, thus enabling the orientation of the neurosurgery probe to be adjusted relative to the skull. Screws are used to hold the neurosurgery probe stationary relative to the plate. A ball holder ring holds the ball against the plate. The device has several disadvantages in use, including the fact that it comprises several loose parts (including small screws) and the mechanism fixing the ball in position is a screw which grips the ball. This makes the equipment difficult to handle, and the screw can easily be lost. The devices for securing the ring to the skull are not adequate to ensure the absence of relative movements. The main drawback of this device is that the radius of action is severely restricted, since the ball's central point is located outside the area defined by the cranium.

U.S. Pat. No. 4,681,103 discloses a guiding device for ultrasound adjustment of surgical instruments. The device consists of an adaptor housing which is securely screwed to the skull and which has a longitudinal opening through which instruments are passed. For screwing purposes the device is provided with a gripping surface which is held by the fingers. Such an attachment mechanism makes the device difficult to secure on those areas of the head where there is very little room round the adaptor housing (e.g. near shoulders and at the back of the head).

At the same time it is difficult to exercise sufficient force when screwing into the compact outer bone layer of the cranium. The ball's optimal position is an abutment against the surface of the brain, since the closer to the surface of the brain the centre of the ball is located, the smaller the opening in the skull which is necessary to reach a large area of the skull. In the adaptor housing described in U.S. Pat. No. 4,681,103 the position of the attachment threads in the housing and the position of the ball in the socket are such that the ball is not located in the said optimal position. In addition to this the ball's diameter is the same size as the longitudinal opening. The combination of these features means that the angular area which is available when using this known device is no greater than 60°. Moreover, several parts are required to lock the ball in a specific position, leading to a reduction in reliability.

U.S. Pat. No. 4,809,694 shows a biopsy guide including a cranial tap, a spherical member and a retaining structure attachable to the tap to immobilize the spherical member in a desired orientation. The cranial tap places the spherical member quite "far" from the skull surface and this leads to a reduced working range in the actual brain zone. The retaining structure contributes also to limit the instrument's working range by limiting the angle of movement of the instrument in the area above the spherical member. This device is thus not satisfactory because the working range is greatly reduced. Besides the device contains several small pieces and this is not advisable because it leads to problems in operation. It is also known to employ ball joints for securing equipment in a specific position relative to the brain (U.S. Pat. No. 4,681,103). In this case soft or collapsible balls are employed which, when secured in a specific angular position, clamp the tubes together, thereby securing the tubes' angular position. However, these devices do not permit any further movement of the tubes relative to the ball. Thus they do not permit any advance adjustment of the ball's angular position before the equipment is passed through it.

These and other problems associated with the known solutions are solved by means of the device and method according to the invention. The device according to the invention comprises a holder and a fixing key, wherein the holder comprises a lower ring for receiving a ball which will form a ball joint, and an upper ring for locking the ball in a specific position, where the ball has a channel for insertion of medical instruments, and where the lower ring has an external threaded surface for direct screwing to an area of a patient's skull. The device is characterized in that the ball's central point, and thereby the ball joint's fulcrum is arranged for positioning on a level with the patient's cranium by means of a groove-like or curved surface on the holder which forms an abutment for the ball. The invention also concerns a method for adjustment of different stereotactically and endoscopically located equipment, including pharmaceutical agents, by means of the holder, characterized by:

localising a point on the skull, making a burr hole attaching the holder's lower ring to the wall of the formed burr hole by means of the key, placing the ball on the lower ring in such a manner that the ball's central point is on a level with the patient's cranium, attaching the upper ring to the lower ring without locking the ball, passing a stereotactic pointer through the ball in order to adjust direction, locking the ball in a specific angular position, replacing the stereotactic pointer with implantable equipment, such as a drain, an electrode, etc., or with temporarily introduceable equipment, such as an endoscope, a biopsy needle etc.

The invention also concerns the application of the device and the method for:

biopsy taking, puncture of, e.g., cysts, abscesses and other expansive processes, puncture of the ventricle system by placing drains and equipment, placing of markers, isotopes and biological or other material, such as neuroactive cells, placing of electrodes or other equipment for recording/stimulation of the brain.

The holder's lower ring is equipped with grooves for co-operation with protrusions in the fixing key which is employed for screwing the ring's threaded surface on to and off an area of the skull. The use of the fixing key, has several advantages including the fact that it permits great force to be exerted, thus securing the ring in the compact outer bone layer of the cranium. In addition to this the use of a key gives access to difficult areas (the key is long and narrow and does not require extra space round the securing ring). The equipment is designed in such a manner that the ball's lower part is on a level with the surface of the dura. This ensures the best possible accessibility for reaching various brain structures through a small burr hole.

The holder's upper ring is equipped with notches on the circumference whose object is to obtain a good grip for securing the upper ring to the lower ring, thereby facilitating correct positioning. Both the upper and the lower ring are provided with inclined surfaces which permit angular placement of the ball in a large angular area (up to approximately 74°).

The holder according to the invention is simple to use. It does not require complicated instruments to attach it to the skull. The holder consists of only three parts which are easy to assemble and to disinfect.

Since the channel in the ball is unaltered when the ball is locked and unlocked, the holder permits previous adjustment of an angular position, for example by inserting a pointer in the channel, removing the pointer without losing the angular position, and introducing a surgical instrument which will only be restricted in angular position, but which will still be able to rotate in the channel and also be moved in the channel's axial direction.

In a preferred embodiment the ball is equipped with a centrally extending cast-in tube for guiding the instruments through the ball, and the tube's diameter is considerably smaller than the ball's diameter. Together with the rings' inclined planes, this helps to give the instrument a large range of motion in the angular direction. In a preferred embodiment the channel has a lower section with a smaller cross section, which ensures that the orientation equipment (which is used for adjusting the direction) is stopped in the equatorial plane of the ball where the latter abuts against or a few millimetres above the surface of the brain. Where the channel does not have a lower section with a smaller cross section, but has a constant inner cross section, it may be supplied with stoppers on the upper side which will abut against corresponding stoppers in the pointer instruments, thereby restricting the instrument's movement in depth. The tube projects out of the ball towards the environment, thereby increasing the guiding effect on the instruments.

The support for the instruments which is composed of the ball's through-going opening or the tube surrounds the point of the instrument along a major part of the length of the point as close as possible up to the tip of the point.

Since the insertion channel in the casing and the channel through the ball ends right down on the surface of the dura, all instruments which are introduced are ensured support as far as possible up to the brain. The free tip of the instruments is therefore as short as possible. This reduces the risk of navigation error compared with insertion systems which are located further from the surface of the brain.

During use the holder may, e.g., be further supplied with an adaptor for biopsy needles provided inside the tube, which adaptor is externally adapted to the internal diameter of the insertion sleeve which is connected to the ball and which is internally adapted to the circumference of the instruments which have to be used. Two locks/stoppers are mounted at the correct length along the equipment (e.g. biopsy needles) which have to be inserted into the brain. These locks will abut against a collar on top of the adaptor which is adapted to the individual instrument. By this means equipment is prevented from being inserted deeper into the brain than planned.

In an advantageous embodiment the tube and the adaptor comprise identification means for connecting them to different equipment.

Since it can be sufficient to make a hole in the dura which is exactly as large as the instrument which has to be inserted, optimal sterility is guaranteed. Moreover, larger holes in the dura cause the surface of the brain to collapse slightly. This can be eliminated by the use of the invention.

The equipment is so designed that it is easy to remove after electrodes and other equipment which have to project through the skin have been placed inside the brain. In order to unscrew the bottom ring longer lines or drains may be temporarily inserted and project through a channel drilled in the fixing key (not illustrated in the figures). This means that in a preferred embodiment the method according to the invention comprises the following further steps:

removal of the holder's upper ring, removal of the ball, insertion of the implantable/temporarily introduceable equipment in the key through a channel therein, removal of the holder's lower ring, removal of the implantable/temporarily introduceable equipment from the key, while the equipment remains in place in the patient.

The device according to the invention also permits the ball to be removed in an approximately parallel fashion even though it is in the extreme position of the ball joint's movement.

The device according to the invention has a wide range of applications. It can be used amongst other things for:

a) taking biopsies (e.g. tissue samples from tumours and infected brain tissue);

b) puncture of amongst other things cysts, abscesses (pus formations) and other expansive processes;

c) puncture of the ventricle system with placing of drains and equipment (e.g. endoscope);

d) placing of markers (for any subsequent radiation or surgery), isotopes for local radiation) and biological or other material (e.g. neuroactive cells for treatment of, e.g., Parkinson's disease);

e) placing of electrodes or other equipment for recording/stimulation in the brain.

The device and the method according to the invention are otherwise characterized by the features presented in the appended patent claims.

The device will now be described in more detail with reference to an example of an application of the holder and to the accompanying figures in which.

Figure 1:
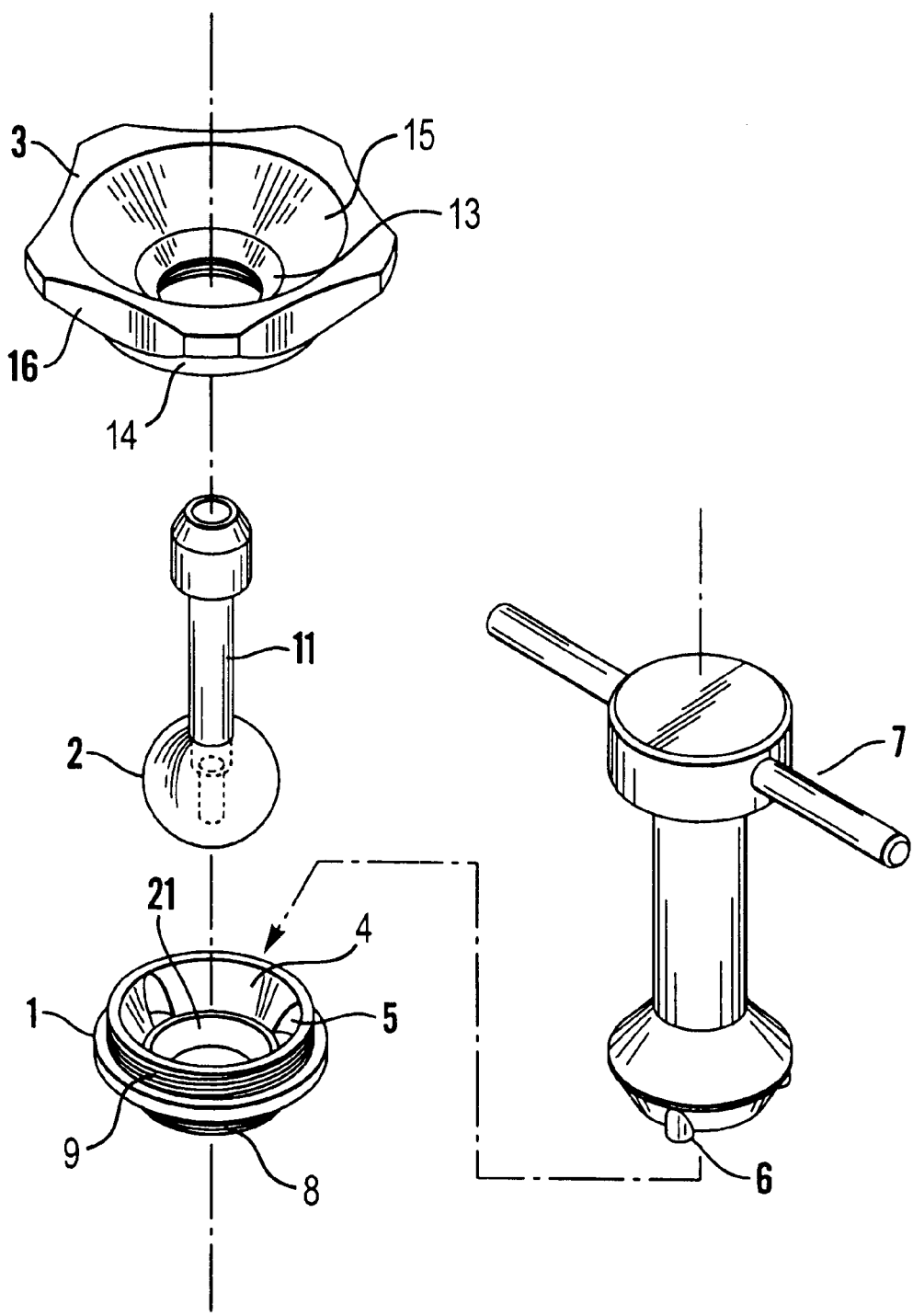
FIG. 1 is a section of a preferred embodiment of the device according to the invention in a dismantled position, illustrating the relative position of the elements

FIG. 1 illustrates the device according to the invention in a dismantled position. The device comprises a holder with a lower ring 1 for placing a ball 2, with notches 5 for co-operation with the protrusions 6 in a fixing key 7, and with two external threaded surfaces: a lower surface for attaching the ring to the skull and an upper surface for locking the ball 2. The lower ring 1 is further provided with a groove-like or curved surface 21 which forms an abutment for the ball 2.

The ball 2 which will form a ball joint is equipped with a through-going channel for insertion of medical instruments. According to a preferred embodiment the ball is equipped with a cast-in tube 11, which will guide the medical instruments through the ball 2. The holder comprises also an upper ring 3 with a curved surface which surrounds the top of the ball 2 and an internal threaded surface for co-operation with the upper threaded surface in the lower ring 1. The ball 2 can be freely rotated and moved with a conical movement as long as the upper ring is not tightened on the lower ring 1. The upper ring 3 has notches 16 on the circumference, the object of which is to obtain a good grip for attaching the rings 1 and 3 to each other around the ball 2.

Figure 2:
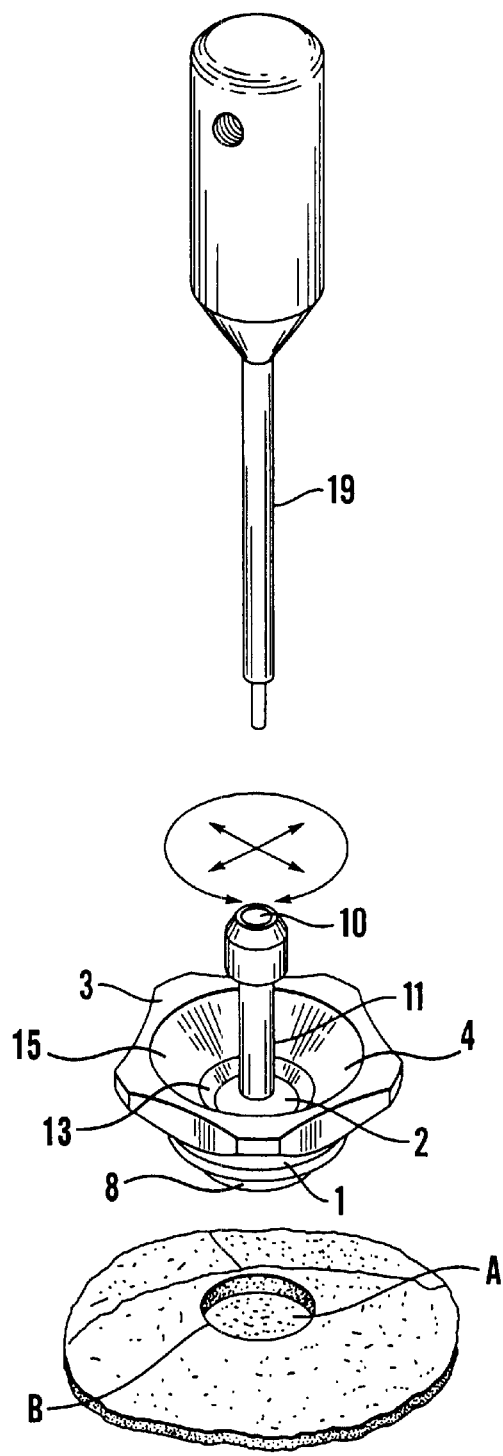
FIG. 2 is a section of the same preferred embodiment of the device according to the invention in an assembled position and also of an instrument for use with the holder.
Figure 3B:
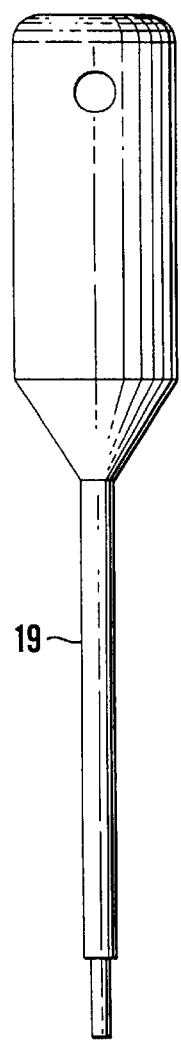
FIGS. 3 and 4 are cross sections of the same preferred embodiment of the device according to the invention.
Figure 3B:
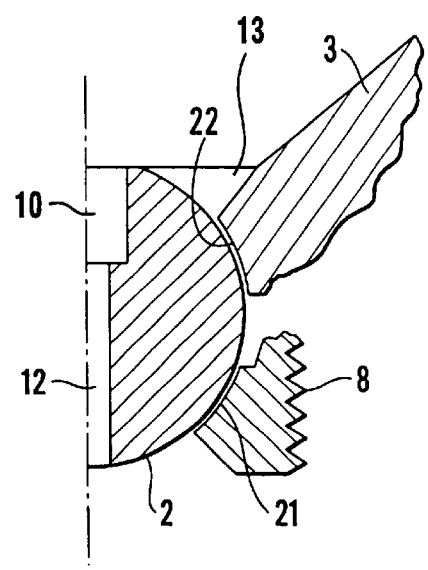
Figure 3A:
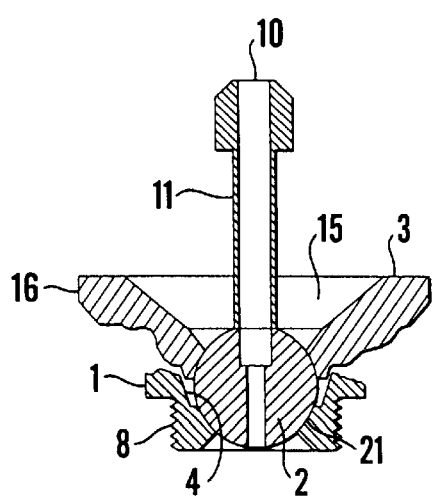
Figure 4:
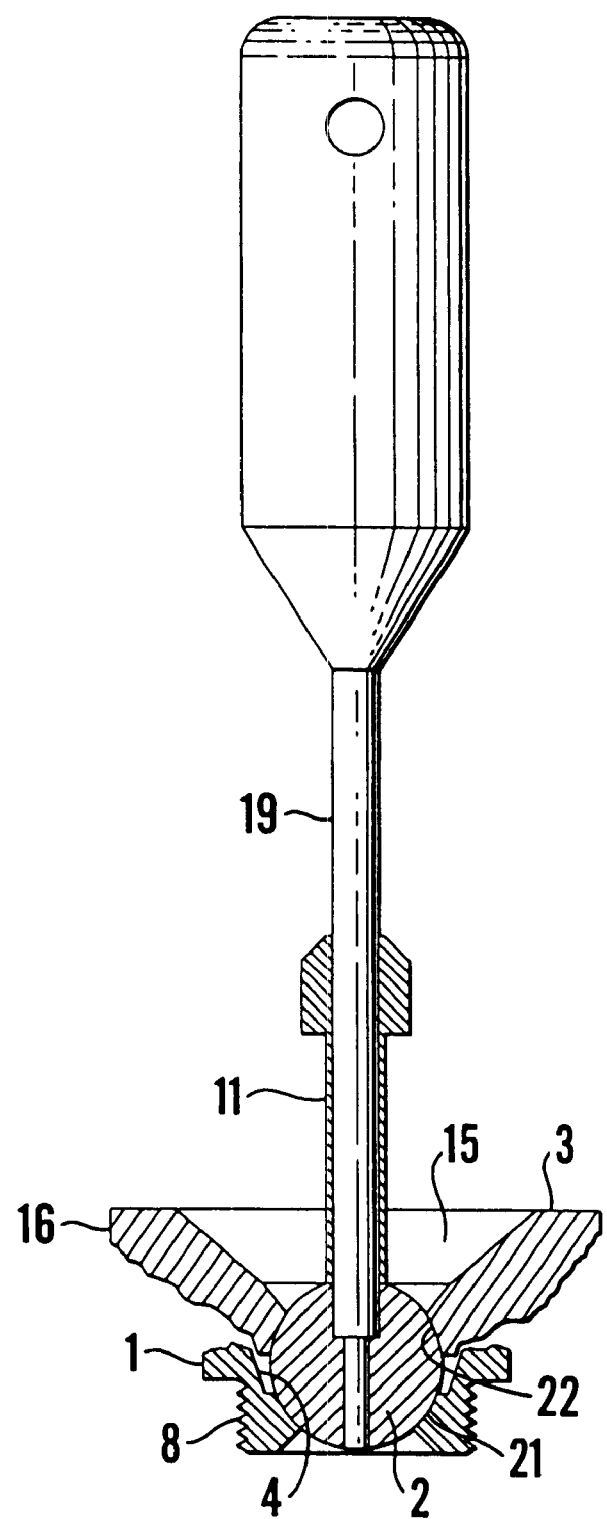
Figure 5:
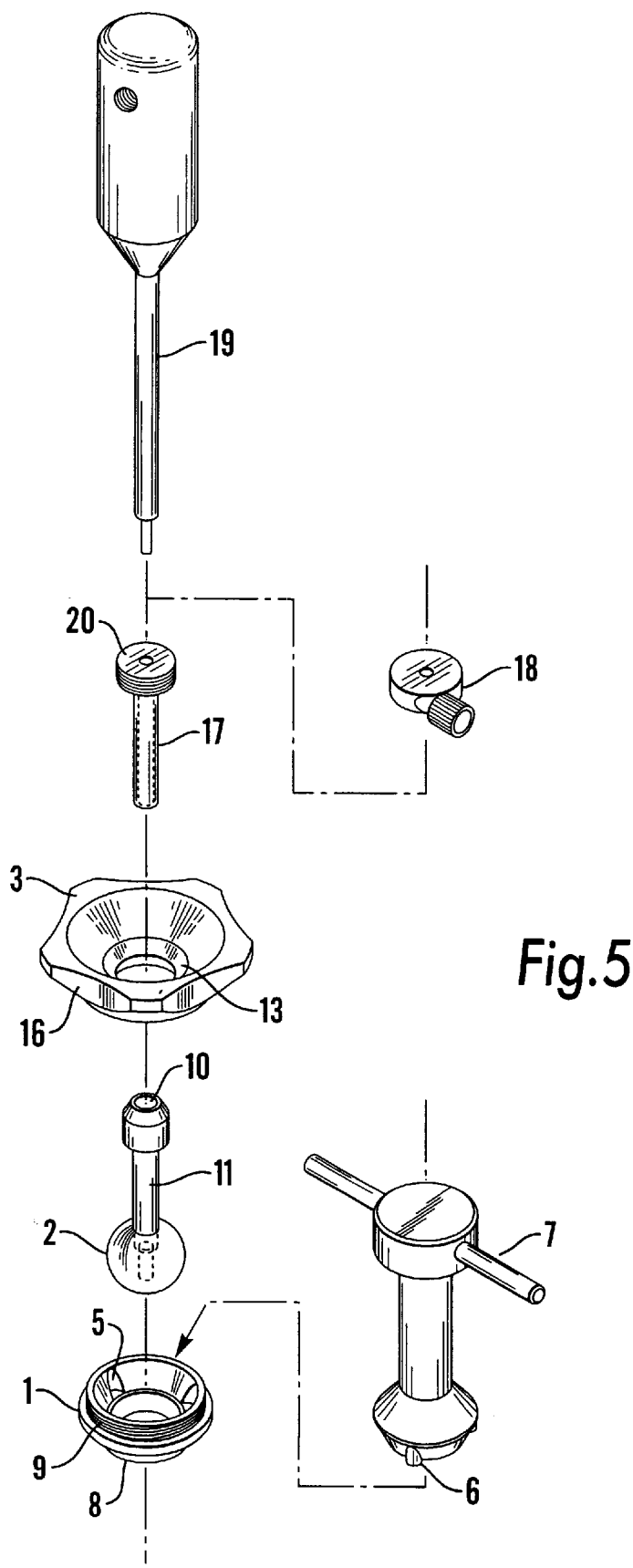
FIG. 5 shows the device according to the invention together with supplementary elements.

FIG. 2 illustrates the device in an assembled position. The figure shows an opening A in the skull, where the lower threaded surface in the lower ring 1 has to be attached, the holder in an assembled position and an instrument 19 for establishment of the ball's 2 angular position. external threaded section 8 and an upper external threaded section 9. The ring comprises also a conical section 4 for ensuring highest possible range of movement for the instrument and a lower groove-like or curved surface 21 for abutment against the ball 2. The ball 2 comprises a through-going channe,l 10 and in a preferred embodiment of the invention, channel 10 has a lower section 12 with a smaller cross section that the rest of the channel, and which, restricts the movements of the instruments which are employed for adjusting the equipment. These instruments will have a part with a larger diameter than the channel's 10 lower section 12 and will thereforebe restricted in the longitudinal movement to the area where the channel is wider than they are (FIG. 4). This ensures that the adjustment instruments do not touch the brain. The upper ring 3 is equipped with an internal threaded section for cooperation with the upper external threaded section 9 in ring 1. Ring 3 has also an upper conical opening 15 whose object is to ensure the best possible range of movement for the instruments, and an upper curved surface 22 for abutment against the ball 2. Reference number 13 denotes a lower edge 13 that establishes a transition between the conical opening 15 and the curved surface 22.

The method for adjusting equipment by means of the device according to the invention will now be illustrated with reference to the drawings. It comprises amongst others the following steps:

by means of pointing equipment (not shown) a point is localised on the skull which is selected as an approach to the area which has to be examined;

a burr hole (opening A, FIG. 2) is made with a conventional "ball drill" (Aesculap, diameter=16 mm);

the lower ring's 1 lower threaded surface 8 is screwed into the wall of the formed burr hole A, by means of the fIxing key 7 with protrusions 6, the ring's 1 notches 5 being adapted to the protrusions (figures); and fixed in the cranium;

the ball 2 is placed on the lower ring 1;

the upper ring 3 is placed on top, and the rings are screwed together, holding the ball 2 between the lower groove like or curved surface 21 and the upper curved surface 22 respectively, the ball 2 is attached as far down as the upper ring 3 is placed on top, and the rings are screwed together, holding the ball 2 between the lower groove like or curved surface 21 and the upper curved surface 22 respectively, the ball 2 is attached as far down as possible towards the cranium in order to ensure the best possible stability and range of movement, thus providing the best possible precision and adjustability;

the tube 11 can be freely maneuvered and rotated as long as the ball 2 is not locked between the rings 1 and 3. The holder permits non-cylindrical equipment to be rotated by means of movement both between adaptor 17 and the tube 11 and in the ball joint 2, this freedom of rotation also allows an image guided probe to acquire separate optimal imaging planes thereby;

a stereotactic pointer 19 is inserted into the tube 11 and stopped where the pointer's tip touches the ball's 2 most distal equatorial plane;

the direction of the tube 11 is adjusted and the depth to the area in which the examination/operation is to be performed is determined;

the ball 2 is locked by tightening ring 3 around ring 1 so that the upper and lower curved surfaces surround and hold the ball 2;

the pointer 19 is withdrawn and set aside so that all unnecessary equipment including holders for fixing soft parts aside—is removed before instruments are inserted into the brain (this ensures the best working conditions for further treatment);

an adaptor 17 which is specially adapted to the equipment which has to be passed down the tube is put in place, the adaptor's end piece 20 preferably being coloured green and projecting, for example, 5 mm above the tube 11;

the equipment which is passed into the adaptor 17 will be stopped when a ring clamp 18 stops against the adaptor's end piece 20;

the distance to the target area within the brain is read off;

the tube's 11 and the adaptor's 17 length (for example 45 mm+5 mm=50 mm) are added;

the ring clamp 18 is attached to a biopsy needle or another instrument (not shown in the figure) which is thereby stopped at the correct depth.

The biopsy needle's locking system preferably has two hinged ring clamps 18 for maximum security (only one is shown in the figure).

In a preferred embodiment of the invention the top part of the tube 11 is coloured red as a warning against inserting any other equipment than the stereotactic pointer tip 19 therein.

In a further preferred embodiment, the fixing key has 7 a centrally extending channel (not shown).

The invention described above represents a universal device which can be employed for many purposes.

In addition to what has been mentioned, the device may also be employed, e.g., as a holder and support for equipment which is moved within the brain. The attachment over the ball joint will ensure the least possible movement of the brain structures under the cranium. In this way care is taken to protect vital brain structures from unnecessary movement, stress and damage. These areas of application are included without departing from the scope of the invention as indicated in the appended patent claims.

What is claimed is:

1. Apparatus for adjusting stereotactically and endoscopically located equipment, comprising;
   a ball having a channel for insertion of medical instruments;
   a holder including a lower ring for receiving the ball for universal positioning adjustment about a central ball fulcrum, and an upper ring for locking the ball in a specific position, the lower ring having an external threaded surface for direct screwing to an area of a patient's cranium;
   a fixing key for securing the lower ring to the cranium; and
   a concave curved surface within the external threaded surface of the lower ring to support the ball so that the fulcrum and lowest point of the ball are located on a level within the cranium.

2. The apparatus of claim 1, wherein the upper ring and the lower ring have conical openings diverging away from the ball.

3. The apparatus of claim 1, wherein the lower ring has an upper threaded surface for co-operation with an internally threaded depending portion of the upper ring.

4. The apparatus of claim 1, wherein the lower ring has grooves for cooperation with protrusions in the fixing key employed for screwing the lower threaded surface of the lower ring into and out of an area of the cranium.

5. The apparatus of claim 1, wherein the upper ring is equipped with notches on the circumference thereof to facilitate gripping to secure the upper ring to the lower ring.

6. The apparatus of claim 1, wherein the upper ring has an upper conical opening.

7. The apparatus of claim 1, wherein the ball has a centrally extending cast-in tube for guiding medical instruments through the ball, the tube projecting from the ball towards the surroundings.

8. The apparatus of claim 7, wherein the diameter of the tube is smaller than the diameter of the ball.

9. The apparatus of claim 7, wherein the tube defines a channel having a lower section of reduced cross section for restricting the range of instrument motion in the tube.

10. The apparatus of claim 7, further including an adaptor for biopsy needles disposed inside the tube and with at least one stopper for biopsy needles disposed on the top of the adaptor.

11. The apparatus of claim 10, wherein the stopper includes at least one hinged ring.

12. The apparatus of claim 10, wherein the tube and the adaptor comprise identification means for connecting them with different equipment.

13. The apparatus of claim 1, wherein the holder and the key employed for screwing the threaded surface of the lower ring to an area of the cranium are designed in such a manner that it is possible to implant equipment which has to project through the skin after the procedure.

14. The apparatus of claim 1, wherein a support for the instruments is composed of the through-going channel in the ball and a tube surrounding the point of the instrument for a major part of the length thereof.

15. The apparatus of claim 1, wherein the key has a drilled channel to permit removal of the lower ring from the cranium while equipment projecting through the ring remains in place.

* * * * *